United States Patent [19]
Dell et al.

[11] Patent Number: 5,434,160
[45] Date of Patent: Jul. 18, 1995

[54] PYRANO[3,2-H]QUINOLINES FOR TREATING RESTENOSIS

[75] Inventors: Colin P. Dell, Dorking; Andrew C. Williams, Camberley, both of England

[73] Assignee: Lilly Industries Limited, Basingstoke, England

[21] Appl. No.: 150,945

[22] Filed: Nov. 12, 1993

[30] Foreign Application Priority Data

Nov. 18, 1992 [GB] United Kingdom .................. 9224169
Feb. 6, 1993 [GB] United Kingdom .................. 9302367

[51] Int. Cl.⁶ .................. A61K 31/44; C07D 491/052
[52] U.S. Cl. ........................................ 514/291; 546/89
[58] Field of Search ............................ 546/89; 514/291

[56] References Cited

U.S. PATENT DOCUMENTS

| | | | |
|---|---|---|---|
| 4,243,674 | 1/1981 | Bindra | 514/454 |
| 4,931,221 | 6/1990 | Heller | 549/389 X |
| 5,093,339 | 3/1992 | Kasama | 514/291 |

FOREIGN PATENT DOCUMENTS 8505031 11/1985 WIPO.

OTHER PUBLICATIONS

McBride "Restenosis after successful coronary angioplasty" New England J. Med. 318 1734–1737 (1988).
Martin et al. "Role of Murine Tumor Models in Cancer Treatment Research" Can Res 46 2189–2192 (1986).
Clarkson et al. "The Role of Individual ..." Ann. N.Y. Aca. Science 454 pp. 28–43 (1985).
Elnagdi, et al., *Naturfoschung B*, 47(4), pp. 572–578 (1992).
Elagamey, et al. *Indian Journal of Chemistry*, 29B, 885–886 (1990).
Elagamey, et al., *Collection Czechoslovak Chem. Commun.*, 53(7), 1534–1538 (1988).
Otto, et al., *Monatshefte fur Chemi*, 110, 115–119 (1979).
Otto, et al., *Monatshefte fur Chemi*, 110, 249–256 (1979).
Otto, et al., *Arch. Pharm.*, 312(6), 548–550 (1979).

Maybridge Chemical Company, Structure List No. 183, May 1989.
Maybridge Chemical Company, Exclusive Listing No. 1187/513684/13279, Nov. 6, 1987.
Maybridge Chemical Company, Exclusive Listing No. 288/513845/13684, Feb. 19, 1988.
Paull, et al., *Cancer Research*, 52, 3892–3900 (1992).
El-Taweel, et al., *Pharmazie*, 45 671–672 (1990).
Khalil, et al., *Bull. Chem. Soc. Jpn.*, 64(2), 668–670 (1991).

*Primary Examiner*—Ceila Chang
*Attorney, Agent, or Firm*—Steven P. Caltrider

[57] ABSTRACT

Pharmaceutical compound of the formula

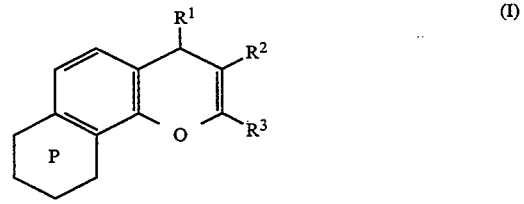

$R^1$ is phenyl or heteroaryl selected from thienyl, pyridyl, benzothienyl, quinolinyl, benzofuranyl or benzimidazolyl, said phenyl and heteroaryl groups being optionally substituted, or $R^1$ is furanyl optionally substituted with $C_{1-4}$ alkyl;

$R^2$ is nitrile, carboxy, —$COOR^4$ where $R^4$ is an ester group, —$CONR^5R^6$ where $R^5$ and $R^6$ are each hydrogen or $C_{1-4}$ alkyl, or $R^7SO_2$— where $R^7$ is $C_{1-4}$ alkyl or optionally substituted phenyl;

$R^3$ is —$NR^8R^9$, —$NHCOR^8$, —$N(COR^8)_2$, —$N=CHOR^8$ where $R^8$ and $R^9$ are each hydrogen or $C_{1-4}$ alkyl, or —$NHSO_2R^{10}$ where $R^{10}$ is $C_{1-4}$ alkyl or optionally substituted phenyl; or (Abstract continued on next page.)

Abstract—continued
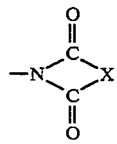
where X is $C_{2-4}$ alkylene; and
the group
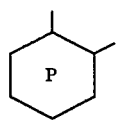
represents a pyridine ring fused to the benzopyran nucleus;
and salts thereof.
7 Claims, No Drawings

PYRANO[3,2-H]QUINOLINES FOR TREATING RESTENOSIS

This invention relates to pharmaceutical compounds, their preparation and use.

The prior art discloses certain pyranoquinolines, as for example the 4H-pyrano [3,2-h] quinolines of Z. H. Khalil et al. Bull. Chem. Soc. Jpn., 64, 668–670 (1991), A. G. A. Elagamey et al. Collection Czechoslovak Chem. Commun., 53(7), 1534–8 (1988), F. M. A. El-Taweel et al. Pharmazie, 45(9), 671–3 (1990), and K. D. Paull et al. Cancer Res., 52(14), 3892–3900 (1992).

We have found that compounds of the following general formula are indicated for use as pharmaceuticals:

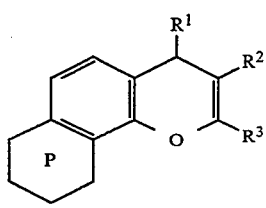

$R^1$ is phenyl or heteroaryl selected from thienyl, pyridyl, benzothienyl, quinolinyl, benzofuranyl or benzimidazolyl, said phenyl and heteroaryl groups being optionally substituted, or $R^1$ is furanyl optionally substituted with $C_{1-4}$ alkyl;

$R^2$ is nitrile, carboxy, —COOR$^4$ where $R^4$ is an ester group, —CONR$^5$R$^6$ where $R^5$ and $R^6$ are each hydrogen or $C_{1-4}$ alkyl, or R$^7$SO$_2$— where $R^7$ is $C_{1-4}$ alkyl or optionally substituted phenyl;

$R^3$ is —NR$^8$R$^9$, —NHCOR$^8$, —N(COR$^8$)$_2$, —N=CHOR$^8$ where $R^8$ and $R^9$ are each hydrogen or $C_{1-4}$ alkyl, or —NHSO$_2$R$^{10}$ where $R^{10}$ is $C_{1-4}$ alkyl or optionally substituted phenyl; or

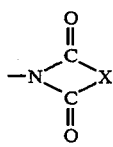

where X is $C_{2-4}$ alkylene; and the group

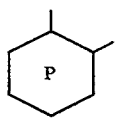

represents a pyridine ring fused to the benzopyran nucleus;
and salts thereof.

The compounds of the invention have been found to be active in tests which show their potential for treatment of immune diseases in which excess cell proliferation or enzyme release play a significant role.

The compounds of formula (I) above are novel with the exception of compounds in which the group

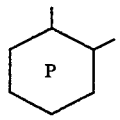

is

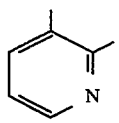

and
(i) $R^1$ is phenyl or phenyl substituted in the para-position with a single chloro, hydroxy or methoxy group, $R^2$ is nitrile, and $R^3$ is —NH$_2$,
(ii) $R^1$ is phenyl or phenyl substituted in the para-position with a single chloro or methoxy group, $R^2$ is —COOC$_2$H$_5$, and $R^3$ is —NH$_2$, or
(iii) $R^1$ is phenyl, $R^2$ is nitrile, and $R^3$ is —NHCOCH$_3$ or —N=CHOC$_2$H$_5$.

A specific example of one of the compounds excluded from this novel group is 2-amino-4-phenyl-4H-pyrano[3,2-h]quinoline-3-carbonitrile.

It will be appreciated that the compounds of the invention can exist in four forms which can be represented by the following structures:

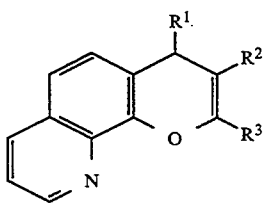

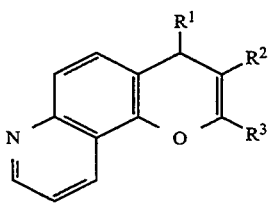

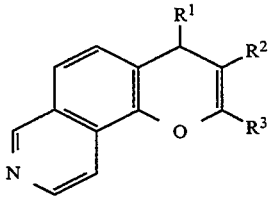

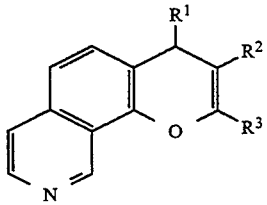

Preferred compounds are those represented by structures (II), (III), and especially (II) and (IV). Novel compounds of structure (II) are subject to the exclusion of certain compounds as specified above.

In the above formula (I), a $C_{1-4}$ alkyl group includes, for example, methyl, ethyl, propyl and butyl, and is preferably methyl or ethyl.

A substituted phenyl group is substituted with one or more, preferably one or two substituents each selected from, for example, halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —COOR$^{11}$ where R$^{11}$ is an ester group, —CONR$^{12}$R$^{13}$ or —NR$^{12}$R$^{13}$ where R$^{12}$ and R$^{13}$ are each hydrogen or $C_{1-4}$ alkyl. When the substituent is —COOR$^{11}$, R$^{11}$ can be, for example, aryl-CH$_2$— such as for instance benzyl, and is preferably $C_{1-4}$ alkyl, especially methyl or ethyl. Substituted naphthyl and heteroaryl groups may be similarly substituted. In addition substituted phenyl includes a phenyl group in which neighbouring atoms are substituted by —O(CH$_2$)$_m$O—, where m is 1, 2 or 3.

When R$^1$ is heteroaryl it is preferably 2-thienyl, 3-thienyl, 2-pyridyl, 3-pyridyl, 4-pyridyl, 2-benzothienyl, 3-benzothienyl, 2-quinolinyl, 3-quinolinyl, 2-benzofuranyl, 3-benzofuranyl, 2-benzidimazolyl, 2-furanyl or 3-furanyl. A naphthyl group is attached at the 1- or 2-position. Such groups can be substituted at any of the available positions, but are preferably unsubstituted.

A preferred value of R$^1$ is optionally substituted phenyl, preferably phenyl with a single substituent, especially nitro, trifluoromethyl, $C_{1-4}$ alkoxy, especially methoxy, or —COOR$^{11}$ where R$^{11}$ is $C_{1-4}$ alkyl, especially methyl. A preferred group of compounds is one in which R$^1$ is phenyl substituted with a single substituent in the meta-position, such substituent being any of the substituents listed above as examples of substituents on the phenyl group.

The group R$^2$ is preferably nitrile. When R$^2$ is —COOR$^4$, R$^4$ can be any ester group, for example, aryl-CH$_2$— such as benzyl, and is preferably $C_{1-4}$ alkyl, especially methyl or ethyl.

The group R$^3$ is preferably —NR$^8$R$^9$, and especially —NH$_2$.

Preferred compounds are those in which R$^1$ is optionally substituted phenyl, R$^2$ is nitrile and R$^3$ is —NH$_2$.

A preferred group of compounds according to formula II above is one in which R$^1$ is phenyl substituted with a single substituent in the meta-position, R$^2$ is nitrile and R$^3$ is —NH$_2$.

A further preferred group of compounds according to formula II is one in which R$^1$ is phenyl substituted with a nitro, trifluoromethyl, methoxy or —CO$_2$Me, R$^2$ is nitrile and R$^3$ is —NH$_2$.

It will be appreciated that when, for example, R$^2$ is —COOH, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

It will be appreciated that the pyridine nucleus also affords an opportunity for the preparation of acid addition salts. Acid addition salts can be prepared from suitable acids, such as inorganic acids, for example hydrochloric, hydrobromic, nitric, sulphuric or phosphoric acids, or organic acids, such as organic carboxylic acids, for example glycollic maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

It will be appreciated that the compounds of the invention contain an asymmetric carbon atom which gives rise to enantiomers. The compounds are normally prepared as racemates and can conveniently be used as such but individual enantioners can be isolated by conventional techniques if so desired. Such racemates and individual enantiomers form part of the present invention.

The invention also comprises a process for producing a compound of formula (I) above, which comprises (1) reacting a compound of the formula

with a compound of the formula

to give a compound of formula (I) in which R$^3$ is —NH$_2$, or (2) converting a compound of the formula

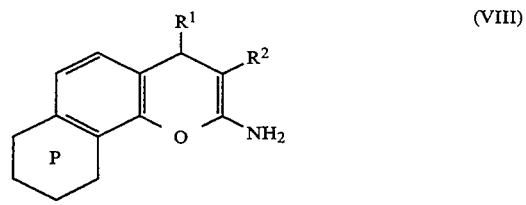

to a compound of formula (I) in which R$^3$ is —NR$^8$R$^9$, —NHCOR$^8$, —N(COR$^8$)$_2$, —N=CHOR$^8$, —NHSO$_2$R$^{10}$, or

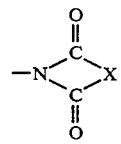

With regard to process variant (1), the reaction is preferably carried out at a temperature of from 0° C. to 100° C. and in the presence of an organic solvent, such as for example ethanol. Compounds of formula (VI) are known or can be readily synthesized by known methods.

The reactants of formula (VII) can be prepared by reacting the appropriate nitrile of the formula $R^2CH_2CN$ with an aldehyde of the formula $R^1CHO$ preferably at a temperature of from 20° C. to 100° C. in the presence of an organic base as catalyst such as, for example, piperidine and in the presence of an organic solvent, such as for example ethanol. The nitrile and aldehyde reactants are known compounds or can be made by methods known in the art.

With regard to process (2), the free enamine can be prepared by reaction (1) and subsequently converted to compounds in which $R^3$ takes other values. For example, the free amino group can be alkylated with reagents of formula $R^8X$ or $R^9X$ where X is halogen, to give the mono- or di-alkylated product. Similarly the amino group can be acylated with an acylating reagent of formula $R^8COX$ or $(R^8CO)_2O$ to give compounds in which $R^3$ is $-NHCOR^8$ or $-N(COR^8)_2$. Compounds in which $R^3$ is $-N=CHOR^8$ are prepared by reaction with the appropriate trialkyl orthoformate, and those in which $R^3$ is $-NHSO_2R^{10}$ by reaction with a sulphonyl halide of formula $R^{10}SO_2X$.

As mentioned above, the compounds have pharmaceutical activity. They have an antiproliferative effect on cell division, and are thus indicated for use in the treatment of diseases where excess cell proliferation or enzyme release is an important aspect of the pathology.

For example, the compounds of the invention inhibit the natural proliferation of 3T3 fibroblasts at $IC_{50}$ concentrations of below 10 μmolar.

Furthermore, the compounds have been shown to modify the immune response by inhibiting concanavalin A-induced T-cell proliferation in the test described by Lacombe P. et al, FEBS, 3048, 191, 227–230.

The compounds also inhibit cell proliferation in an NS-1 murine B-lymphoma line, and phorbol ester-stimulated plasminogen activator synthesis in bovine retinal capillary endothelial cells.

Inhibition of macrophage-conditioned medium induced neutral protease release in chondrocytes has also been observed in the test described by K. Deshmukh-Phadke, M. Lawrence and S. Nanda, *Biochem. Biophys. Res. Commun.*, 1978, 85, 490–496.

Such properties show that the compounds have potential in the treatment of a wide range of diseases, such as for example rheumatoid arthritis, atherosclerosis, cirrhosis, fibrosis and cancer, and for the treatment of auto-immune diseases, such as for example systemic lupus, and in the prevention of graft rejection. They are also indicated for the treatment of osteoarthritis and diabetic complications.

Furthermore, compounds of the invention have been shown to inhibit vascular smooth cell proliferation. This has been demonstrated by using cultured smooth cells derived from rabbit aortae, proliferation being determined by the measurement of DNA synthesis. Cells are obtained by explant method as described in Ross, J. of Cell Bio. 50:172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 μg ml streptomycin, 1 μC/ml $^3$H-thymidine, 20 ng/ml platelet-derived growth factor and varying concentrations of the compounds. Stock solution of compounds are prepared in dimethyl sulphoxide and then diluted to appropriate concentration (0.01–10 μg/ml) in the above assay medium. Cells are then incubated at 37° C. for 24 hours under 5% $CO_2$/95% air. At the end of 24 hours, the cells are fixed in methanol. $^3$H thymidine incorporation in DNA was then determined by scintillation counting as described in Bonin et al., Exp. Cell Res. 181:475–482 (1989).

Inhibition of smooth muscle cell proliferation by the compounds of the invention is further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 μg/ml streptomycin. After 24 hours, the cells are attached, the medium is replaced with DMEM containing 2% platelet poor plasma, 2 mM L-glutamine, 100 U/ml penicillin, 100 μg/ml streptomycin, 40 ng/ml platelet-derived growth factor and indicated concentrations of the compounds. Cells are allowed to grow for four days. Cells are treated with trypsin and number of cells in each cultures is determined by counting using a ZM-Coulter counter.

Activity in the above tests indicates that the compounds of the invention are of potential in the treatment of restenosis, which is characterised by the migration and proliferation of smooth muscle cells in response to injury.

Thus the invention also includes a pharmaceutical composition comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. When the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl, cellulose, methyl- and propyl-hydroxybenzoate, talc, magnesium stearate and mineral oil. The compositions of the injection may, as is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 10 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples.

EXAMPLE 1

A suspension of malononitrile (7.52 g) and 3,4-dimethoxybenzaldehyde (18.95 g) in ethanol (100 ml) was warmed to reflux temperature with stirring. The orange solution was removed from the heat and piperidine (0.5 ml) added down the condenser. Once the vigorous reaction had subsided, the reaction mixture was reheated to reflux temperature and this maintained for 35 minutes. Copious quantities of a bright yellow solid had appeared by this time. The mixture was cooled in an ice bath for 10 minutes and the yellow solid filtered off, washed with ethanol and ether and dried in vacuo at 70° C. yielding 3,4-dimethoxy benzylidenemalononitrile, m.p.137° C.

The following compounds were prepared in a similar manner:

3-Nitrobenzylidenemalononitrile, m.p. 108° C.
3-Methoxybenzylidenemalononitrile, m.p. 102° C.
3-Carbomethoxybenzylidenemalononitrile, m.p. 125° C.
3-Trifluoromethylbenzylidenemalononitrile, m.p. 81° C.
3,4-Dichlorobenzylidenemalononitrile, m.p. 154° C.

EXAMPLE 2

To a stirred suspension of 5-hydroxyisoquinoline (2.90 g) and 3,4-dimethoxy benzylidenemalononitrile (4.28 g) in ethanol (11 ml) was added dropwise piperidine (1.70 g). The suspension was then heated at reflux temperature for one hour forming a red solution. This was then allowed to cool to room temperature, depositing a brown solid. This was filtered off and washed with ethanol and ether and dried in vacuo at 60° C., yielding 2-amino-4-(3,4-dimethoxyphenyl)- 4H-pyrano[2,3-f]isoquinoline-3-carbonitrile as a yellow-brown solid, m.p. 225°–228° C.

The following compounds were prepared in a similar manner:

2-Amino-4-(3,4-dichlorophenyl)-4H-pyrano[2,3-f] isoquinoline-3-carbonitrile, m.p. 215°–218° C.
2-Amino-4-(3-methoxyphenyl)-4H-pyrano[2,3-f] isoquinoline-3-carbonitrile, m.p. 223°–224° C.
2-Amino-4-(3-nitrophenyl)-4H-pyrano[2,3-f] isoquinoline-3-carbonitrile, m.p. 239°–243° C. 2-Amino-4-(3-trifluoromethylphenyl)-4H-pyrano[2,3-f] isoquinoline-3-carbonitrile, m.p. 117°–118° C.
Methyl 3-(2-amino-3-cyano-4H-pyrano{2,3-f] isoquinolin-4-yl) benzoate, m.p.229°–230° C.

EXAMPLE 3

A stirred suspension of 8-hydroxyquinoline (2.90 g) and 3,4-dimethoxy benzylidenemalononitrile(4.28 g) in ethanol (15 ml) was treated with piperidine (1.70 g) and the suspension stirred at room temperature for one hour. This mixture was then heated at reflux for 90 minutes. The red solution was then allowed to cool to room temperature overnight. The precipitated orange solid was filtered off and washed with ethanol and ether and dried in vacuo at 60° C., yielding 2-amino-4-(3,4-dimethoxyphenyl)-4H-pyrano[3,2-h]quinoline-3-carbonitrile as a tan solid, m.p. 118°–120° C.

The following compounds were prepared in a similar manner.

2-Amino-4-(3,4-dichlorophenyl)-4H-pyrano[3,2-h]quinoline-3-carbonitrile, m.p. 218°–222° C.
2-Amino-4-(3-methoxyphenyl)-4H-pyrano[3,2-h]quinoline-3-carbonitrile, m.p. 190°–192° C.
2-Amino-4-(3-nitrophenyl)-4H-pyrano[3,2-]quinoline-3-carbonitrile, m.p. 198°–200° C.
2-Amino-4-(3-trifluoromethylphenyl)-4H-pyrano[3,2-h]quinoline-3-carbonitrile, m.p. 228°–231° C.
Methyl 3-(2-amino-3-cyano-4H-pyrano[3,2-h]quinolin-4-yl) benzoate, m.p.208°–210° C.

EXAMPLE 4

A suspension of 5-hydroxyquinoline (703 mg) and 3-trifluoromethyl benzylidenemalononitrile (1.07 g) in ethanol (5 ml) was stirred and treated with piperidine (410 mg). The red solution was stirred at room temperature overnight and then concentrated in vacuo. The residue was chromatographed on florisil with dichloromethane as eluant, yielding 188 mg of 2-amino-4-(3-trifluoromethyl)-4H-pyrano[2,3-f]quinoline-3-carbonitrile as a cream solid, m.p. 167°–168° C.

The following compounds were prepared in a similar manner.

2-Amino-4-(3,4-dichlorophenyl)-4H-pyrano[2,3-f]quinoline-3-carbonitrile, m.p. 223°–228° C.
2-Amino-4-(3-methoxyphenyl)-4H-pyrano[2,3-f]quinoline-3-carbonitrile, m.p. 218°–222° C.
2-Amino-4-(3-nitrophenyl)-4H-pyrano[2,3-f]quinoline-3-carbonitrile, m.p. 200°–202° C.
2-Amino-4-(3,4-dimethoxyphenyl)-4H-pyrano[2,3-f]quinoline-3-carbonitrile, m.p. 160°–163° C.
Methyl 3-(2-amino-3-cyano-4H-pyrano[2,3-f]quinolin-4-yl) benzoate, m.p.203°–206° C.

EXAMPLE 5

Soft Gelatin Capsule

Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 6

Hard Gelatin Capsule

Each capsule contains:

| | |
|---|---|
| Active ingredient | 50 mg |
| PEG 4000 | 250 mg |

The PEG 4000 is melted and mixed with the active ingredient. Whilst still molten the mixture is filled into capsule shells and allowed to cool.

EXAMPLE 7

Tablet

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

EXAMPLE 8

The concanavalin A response of rat spleen cells was used as a primary in vitro assay to determine the activity of the compounds of the invention. Many methods for the determination of concavalin A response are described in the literature. The method employed was similar to that described by Lacombe P. et al., FEBS 3048 191, 227-230. We used $2 \times 10^5$ cells per culture well, and concanavalin A was employed at 1 μg/ml. 2-Mercaptoethanol was a requirement ($2 \times 10M^{-5}$) and 0.25 μCi of tritiated thymidine was added six hours before cell harvesting.

All of the compounds of the invention disclosed in Examples 2 to 4 inhibited cell proliferation and had an $IC_{50}$ in this test of less than 5 μM.

We claim:

1. A compound of the formula:

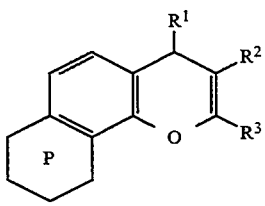

$R^1$ is phenyl or heteroaryl selected from 2-pyridyl, 3-pyridyl, or 4-pyridyl, said phenyl and heteroaryl groups being optionally substituted, or $R^1$ is furanyl optionally substituted with $C_{1-4}$ alkyl;
$R^2$ is nitrile;
$R^3$ is —$NR^8R^9$ where $R^8$ and $R^9$ are each hydrogen or $C_{1-4}$ alkyl; and
the group

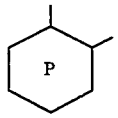

represents a pyridine ring fused to the benzopyran nucleus;
with the exception of compounds in which the group

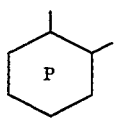

is

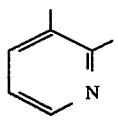

and
(i) $R^1$ is phenyl or phenyl substituted with a single chloro, hydroxy or $C_1$-$C_4$ alkoxy, $R^2$ is nitrile, and $R^3$ is —$NH_2$;
and salts thereof.

2. A compound of formula (I) as defined in claim 1, which has the structure:

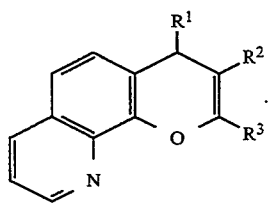

3. A compound of formula (I) as defined in claim 1, which has the structure:

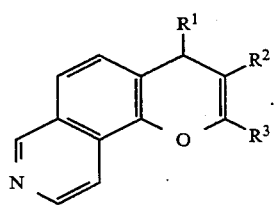

4. A compound according to claim 1 in which $R^1$ is optionally substituted phenyl.

5. A compound according to claim 2 in which $R^1$ is phenyl substituted with a single substituent in the meta-position, $R^2$ is nitrile and $R^3$ is —$NH_2$.

6. A pharmaceutical formulation comprising a pharmaceutically-acceptable diluent or carrier and a compound of the formula:

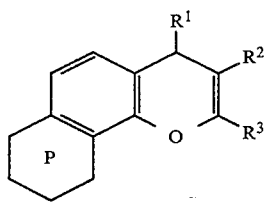 (I)

$R^1$ is phenyl or heteroaryl selected from 2-pyridyl, 3-pyridyl, or 4-pyridyl, said phenyl and heteroaryl groups being optionally substituted, or $R^1$ is furanyl optionally substituted with $C_{1-4}$ alkyl;

$R^2$ is nitrile;

$R^3$ is $-NR^8R^9$ where $R^8$ and $R^9$ are each hydrogen or $C_{1-4}$ alkyl; and the group

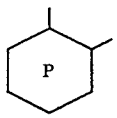

represents a pyridine ring fused to the benzopyran nucleus;

with the exception of compounds in which the group

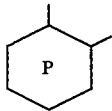

is

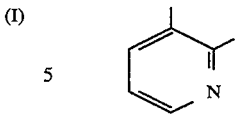

and (i) $R^1$ is phenyl or phenyl substituted with a single chloro, hydroxy or $C_1-C_4$ alkoxy, $R^2$ is nitrile, and $R^3$ is $-NH_2$;

or a pharmaceutically-acceptable salt thereof.

7. A method of treating an animal, including a human, suffering from or susceptible to restenosis, which comprises administering an effective amount of a compound of the formula:

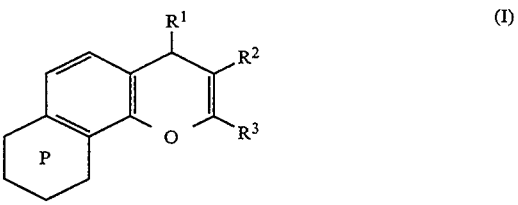 (I)

$R^1$ is phenyl or heteroaryl selected from 2-pyridyl, 3-pyridyl, or 4-pyridyl, said phenyl and heteroaryl groups being optionally substituted, or $R^1$ is furanyl optionally substituted with $C_{1-4}$ alkyl;

$R^2$ is nitrile;

$R^3$ is $-NR^8R^9$ where $R^8$ and $R^9$ are each hydrogen or $C_{1-4}$ alkyl; and the group

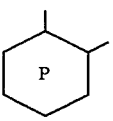

represents a pyridine ring fused to the benzopyran nucleus.

* * * * *